United States Patent [19]

Traxler et al.

[11] Patent Number: 4,916,126
[45] Date of Patent: Apr. 10, 1990

[54] DIACYL DERIVATIVES OF 4-(TRIALKYLBENZYL)-PIPERAZINYL COMPOUNDS

[75] Inventors: Peter Traxler, Schönenbuch; Klaus Müller, Ettingen; Wilhelm Kump, Biel-Benken, all of Switzerland

[73] Assignee: Ciba-Geigy Corporation, Ardsley, N.Y.

[21] Appl. No.: 270,701
[22] PCT Filed: Sep. 25, 1987
[86] PCT No.: PCT/CH87/00123
  § 371 Date: Nov. 14, 1988
  § 102(e) Date: Nov. 14, 1988
[87] PCT Pub. No.: WO89/02894
  PCT Pub. Date: Apr. 6, 1989
[51] Int. Cl.$^4$ ............... C07D 498/08; A61K 31/399
[52] U.S. Cl. ........................................ 514/183; 540/459
[58] Field of Search ........................... 540/459; 514/183
[56] References Cited

U.S. PATENT DOCUMENTS

| | | | |
|---|---|---|---|
| 3,342,810 | 9/1967 | Maggi | 540/458 |
| 3,524,845 | 8/1970 | Bickel et al. | 540/458 |
| 3,644,337 | 2/1972 | Bickel et al. | 540/458 |
| 3,796,798 | 7/1987 | Lancini | 540/458 |
| 4,002,752 | 1/1977 | Cricchio et al. | 540/458 |
| 4,002,754 | 1/1977 | Cricchio | 540/458 |
| 4,005,077 | 1/1977 | Bickel et al. | 540/459 |
| 4,193,920 | 3/1980 | Konstantinova et al. | 540/458 |
| 4,353,826 | 10/1982 | Bickel et al. | 540/459 |
| 4,551,450 | 11/1985 | Traxler | 540/458 |
| 4,585,589 | 4/1986 | Malabarba | 540/458 |
| 4,681,938 | 7/1987 | Traxler | 540/458 |
| 4,774,237 | 9/1988 | Ueno et al. | 540/457 |

FOREIGN PATENT DOCUMENTS

| | | | |
|---|---|---|---|
| 133887 | 8/1985 | European Pat. Off. | 540/459 |
| WO87/02361 | 4/1987 | PCT Int'l Appl. | 540/458 |

OTHER PUBLICATIONS

CA 94: 132053v (1981).
CA 80: 104107h (1974).
CA 91: 68719a (1979).
Burger's Med. Chem., 4th Edit., Part II, pp. 318-321, 577, 1261 (1979).
Per Flatberg et al., Arzneimittal und ihr Anwendung, Fabritius, Oslo, 1974, S. 261-262.

*Primary Examiner*—Robert T. Bond
*Attorney, Agent, or Firm*—Irving M. Fishman

[57] ABSTRACT

Compounds of the formula

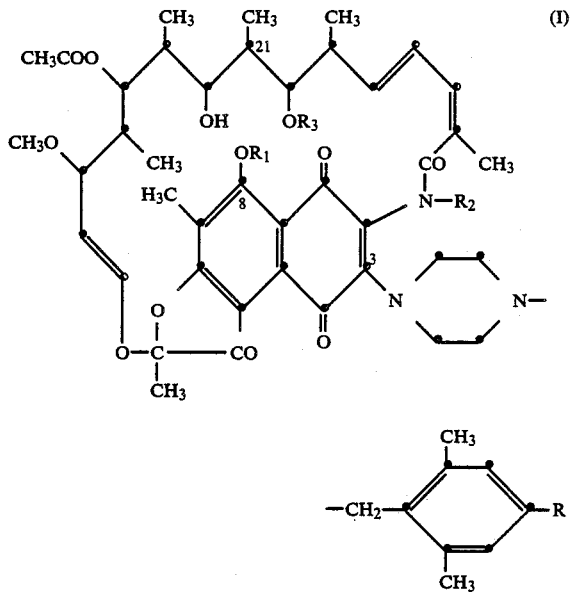

in which R represents lower alkyl, $R_1$ represents tri-lower alkylmethylcarbonyl, and one of the radicals $R_2$ and $R_3$ represents tri-lower alkylmethylcarbonyl and the other represents hydrogen, and salts thereof, exhibit hypo-lipidaemic properties.

14 Claims, No Drawings

DIACYL DERIVATIVES OF 4-(TRIALKYLBENZYL)-PIPERAZINYL COMPOUNDS

The present invention relates to novel diacyl derivatives of rifamycins that carry a substituted 1-piperazinyl radical in the 3-position, namely 8-O,N- and 8-O,21-O-diacyl derivatives of rifamycin S compounds of the formula

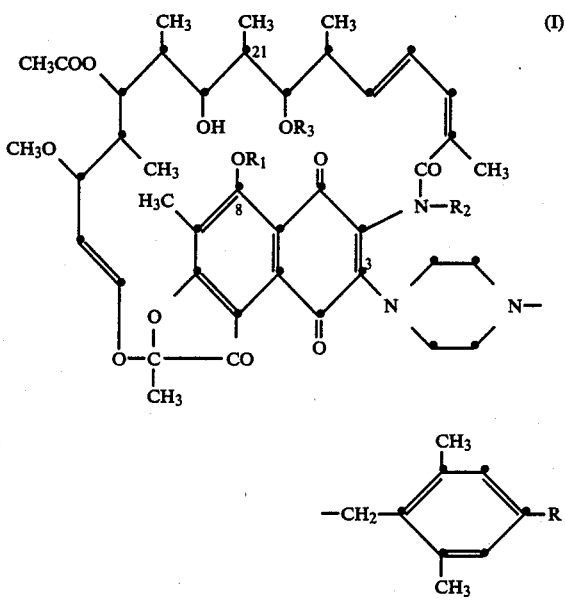

in which R represents lower alkyl, $R_1$ represents tri-lower alkylmethylcarbonyl, and one of the radicals $R_2$ and $R_3$ represents tri-lower alkylmethylcarbonyl and the other represents hydrogen, to their salts, and to mixtures of isomeric compounds of the formula I or their salts.

The invention relates also to processes for the manufacture of compounds of the formula I and their salts, to pharmaceutical preparations containing them, and to the use of these compounds and preparations.

The numbering used herein corresponds to the numbering used, for example, in U.S. Pat. No. 4,005,077.

Lower alkyl R contains preferably up to and including 4 carbon atoms and is, for example, ethyl, propyl, isopropyl, n-butyl, isobutyl or tert.-butyl, but especially methyl.

Lower alkyl radicals in a tri-lower alkylmethylcarbonyl radical normally contain up to and including 4, preferably up to and including 2, carbon atoms and especially one carbon atom, and are, inter alia, n-propyl, isopropyl, n-butyl or tert.-butyl, especially ethyl and more especially methyl.

In the compounds of the formula I, the radicals $R_1$ and $R_2$ or $R_3$ preferably have identical meanings.

Non-acylated rifamycin S compounds that have, in the 3-position, a piperazino group substituted in the 4-position are known. For example, U.S. Pat. No. 4,005,077, especially Example 77, mentions rifamycin derivatives that contain, in the 4-position, a benzyl radical that may be substituted in the aromatic moiety by one or more alkyl radicals having from 1 to 6 carbon atoms, such as 3-(4-benzyl-1-piperazinyl)-rifamycin SV, 3-[4-(4-methylbenzyl)-1-piperazinyl]-rifamycin SV, 3-[4-(2-methylbenzyl)-1-piperazinyl]-rifamycin SV, 3-[4-(3-methylbenzyl)-1-piperazinyl]-rifamycin SV, 3-[4-(4-isopropylbenzyl)-1-piperazinyl]-rifamycin SV, 3-[4-(2,3-dimethylbenzyl)-1-piperazinyl]-rifamycin SV and 3-[4-(4-tert.-butylbenzyl)-1-piperazinyl]-rifamycin SV. Further compounds of that type that have, especially, a 4-(2,6-dimethyl-4-alkylbenzyl)-piperazine radical are described, for example, in the PCT application having the publication No. WO 87/02361. Those compounds are distinguished by an antibiotic action, especially an antitubercular action, which can be demonstrated in vivo in mice and rats and which, as regards the spectrum of action, corresponds approximately to that of the known antitubercular agent, rifampicin.

In contrast, the diacyl compounds of the present invention have, if at all, only a marginal antibiotic action. Surprisingly, however, they have a lipid-reducing action which can be demonstrated in animal experiments, preferably on mammals, for example rats. For example, it is possible to demonstrate the reduction of "very low density", "low density" and "high density" lipoproteins (VLDL, LDL and HDL) in serum in two test procedures, namely in genetically hypercholesterolaemic male rats (procedure A) and normolipaemic rats of both sexes (procedure B).

Albino rats having a body weight of from 180 to 240 g and having free access to normal rat food and drinking water are used, Sprague Dawley derivatives of the strain Tif:RAI in procedure A and animals of the Wistar strain IVa-WI in procedure B. The test compound is administered orally in a polyethylene glycol solution (average molecular weight 400) to groups of from 8 to 10 rats, in procedure A once daily at 8 a.m. for three consecutive days and twice, at 8 a.m. and 4 p.m., on the fourth day, and in the case of procedure B, daily for 5 consecutive days. In experiment A the animals are sacrificed 16 hours, and in experiment B two hours, after the final administration by bleeding from the neck under anaesthesia with ether. The animals are given no food during the 16 hours before they are sacrificed. A 0.05% aqueous ethylenediaminetetraacetic acid solution and a 0.01% aqueous thiomersal solution are added to the combined serum of from 2 to 3 rats. The serum lipoproteins are separated using an unltracentrifuge by means of 24-hour centrifugation at 78,000 g, 78,000 g and 109,000 g in salt solutions having densities of 1.006, 1.040 and 1.21, respectively, and are analysed enzymatically for their content of cholesterol and triglycerides using the test systems supplied, for example, by Miles (Lausanne, Switzerland) and Böhringer (Mannheim, Federal Republic of Germany).

The antibiotic action is ascertained, for example, on the one hand in vitro by determining the mean effective concentration $EC_{50}$ for the inhibition of the RNA polymerase of *Escherichia coli* and by determining the minimum inhibitory concentration MIC in a conventional plate test, and on the other hand in vivo, using infected mice and rats, by determining the $ED_{50}$ (effective dose that ensures the survival of 50% of the experimental animals). There are used as micro-organisms for the present purpose especially *Mycobacterium tuberculosis* TB $H_{37}Rv$ and *Staphylococcus aureus*. In the case of compounds having a lipid-reducing indication, an antibiotic activity is regarded as disadvantageous since it can result in the formation of strains of micro-organisms that are resistant to antibiotics, especially when the compounds are administered over a prolonged period.

In the test methods described above, the compounds according to the invention have a significant hypolipidaemic activity both in the case of a single administration and in the case of repeated administration in a dosage range of from approximately 3 to approximately 50 mg/kg/day; in the above-mentioned tests they are, however, free of any appreciable antibiotic activity.

It can be demonstrated, for example, that, depending on the test procedure, the minimum effective dose of 8-O,N-dipivaloyl-3-[4-(2,4,6-trimethylbenzyl)-1-piperazinyl]-rifamycin S when administered once is from approximately 3 to approximately 10 mg/kg, and a 50–70% reduction in the "LDL fraction" can be achieved by the repeated administration of 30 mg/kg daily. The compound exhibits practically no antibiotic activity; an $EC_{50}$ for the inhibition of the RNA polymerase is not achieved even with 100 μg/ml and the MIC for various pathogenic strains of *Staphylococcus aureus* is approximately 64 μg/ml. Such values are approximately 1000 times higher than concentrations that are normally necessary for a corresponding effect. The compound also proves to be antibiotically inactive in vivo at a single dose of 200 mg/kg using mice infected with *Staphylococcus aureus*. Analogous results are also obtained with the corresponding 8-O,21-O-dipivaloyl compound.

Especially owing to their LDL-reducing action, the compounds according to the invention can be used, for example, as hypolipidaemics for the treatment of hyperlipidaemias, chiefly of the types IIa and IIb, and for the treatment of arteriosclerosis when the presence of hyperlipoproteinaemia constitutes a risk factor.

The present invention relates preferably to compounds of the formula I in which R represents lower alkyl, especially methyl, and in which $R_1$ and $R_2$ represent tri-lower alkylmethylcarbonyl in which lower alkyl contains up to and including 2 carbon atoms, and $R_3$ represents hydrogen, or in which $R_1$ and $R_3$ represent tri-lower alkylmethylcarbonyl in which lower alkyl contains up to and including 2 carbon atoms, and $R_2$ represents hydrogen, and to salts, especially pharmaceutically acceptable salts, thereof, these compounds being in the form of mixtures or preferably in the form of one isomer virtually free of the other isomer, especially in the form of the corresponding 8-O,N-diacylated compound.

The invention relates especially to the compounds of the formula I in which R is methyl, and $R_1$ and $R_2$ represent pivaloyl and $R_3$ represents hydrogen, or $R_1$ and $R_3$ represent pivaloyl and $R_2$ represents hydrogen, and to salts, especially pharmaceutically acceptable salts, thereof, these compounds being in the form of a mixture or in the form of the individual isomers; the corresponding 8-O,N-dipivaloyl derivative is especially preferred.

The novel compounds of the formula I can be manufactured in a manner known per se, for example by treating a compound of the formula

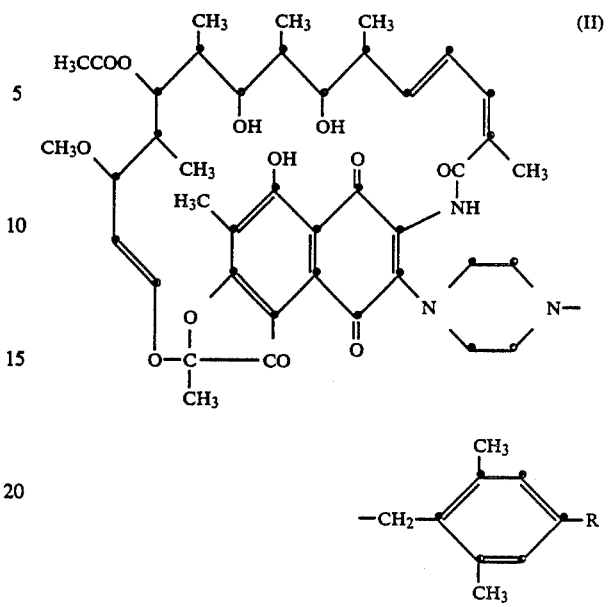

with an acylating agent that introduces a tri-lower alkylmethylcarbonyl radical $R_1$ and $R_2$ or $R_1$ and $R_3$ into position 8, and into position 21 or the ring amide nitrogen atom, and, if desired, separating a mixture of isomers obtained according to the process, and/or converting a salt obtained according to the process into the free compound or into a different salt, and/or converting a free compound obtained according to the process into a salt.

The introduction of the tri-lower alkylmethylcarbonyl radicals $R_1$ and $R_2$ or $R_1$ and $R_3$ into the desired positions can be carried out in a manner known per se using a customary acylating agent suitable for the introduction of such radicals, at least two equivalents of the latter being used. It is possible to use, for example, a corresponding carboxylic acid, if necessary in the presence of a suitable condensation agent, such as dicyclohexylcarbodiimide, but preferably a reactive derivative of such a carboxylic acid, such as an anhydride, especially a mixed anhydride, such as one with an inorganic acid, such as a hydrohalic acid, especially hydrochloric acid or hydrobromic acid (that is to say a corresponding acid halide, for example chloride), or with an organic acid, such as trifluoroacetic acid or a suitable monoester of carbonic acid, or alternatively a symmetric anhydride, or an internal anhydride, that is to say the corresponding ketene.

The derivative of a carboxylic acid employed as acylating agent is preferably used in the presence of a basic agent; a suitable basic agent is especially a non-acylatable organic base, such as a heteroaromatic base, for example pyridine, collidine or quinoline, a tertiary amine, for example triethylamine, N-ethylpiperidine, N-methylmorpholine or 1,4-dimethylpiperazine, or 1,5-diazabicyclo[5,4,0]undec-5-ene.

The acylation reaction is generally carried out in the presence of a solvent or diluent, it being possible to use as such an excess of the acylating agent or the base, for example pyridine, used together with an acylating agent. Other solvents, which can be used, for example, also in admixture with a base, are, for example, non-acylatable organic solvents, such as hydrocarbons, for example pentane, hexane or cyclohexane, halogenated hydrocarbons, for example methylene chloride or chloroform, ethers, for example diethyl ether, ethylene glycol dimethyl ether, tetrahydrofuran or dioxan, acid esters, for example ethyl acetate, and acid amides, for example acetamide or dimethylformamide.

The reaction is generally carried out at room temperature or at slightly elevated temperatures, for example at up to approximately 70° C., the operation being carried out, if necessary, under an inert gas atmosphere. The acylation conditions, especially the amount of acylating agent used, the reaction medium, the temperature and the reaction time, should be so chosen that both acyl groups are introduced, the procedure preferably being in accordance with the methods illustrated in more detail in the Examples. The course of the reaction can advantageously be followed by means of customary analytical methods, especially by means of thin layer chromatography.

The working-up of the reaction product from the reaction mixture obtained according to the process is carried out in a manner known per se, for example by dilution with water and/or optionally by neutralisation or slight acidification (up to approximately pH 3) with an aqueous acid, such as an inorganic or organic acid, for example a mineral acid or, advantageously, citric acid, and by the addition of a water-immiscible solvent, such as a chlorinated hydrocarbon, for example chloroform or methylene chloride, the reaction product passing into the organic phase from which it can be obtained in purified form in customary manner, for example by drying, concentration of the solvent by evaporation and crystallisation and/or chromatography of the residue, or by other customary methods of purification.

The above reaction generally yields a mixture of the two diacylated compounds, the 8-O,N-diacylated compound normally predominating. The mixture can be separated in a manner known per se, for example by means of fractional crystallisation, chromatography, etc., into the desired individual diacyl compounds.

The starting materials of the formula II are known and can be manufactured in a manner known per se; reference is made, for example, to the PCT application having the publication No. WO 87/02361.

The compounds of the present invention can form acid addition salts, especially pharmaceutically acceptable acid addition salts, with inorganic or organic acids. These are, inter alia, hydrohalic acids, for example hydrochloric and hydrobromic acid, sulphuric acid, phosphoric acid, nitric acid or perchloric acid, or aliphatic, carbocyclic (especially aromatic) or heterocyclic carboxylic or sulphonic acids, such as formic, acetic, propionic, succinic, glycolic, lactic, malic, tartaric, citric, fumaric, maleic, hydroxymaleic, pyruvic, phenylacetic, benzoic, p-aminobenzoic, anthranilic, p-hydroxybenzoic, salicylic, p-aminosalicylic or embonic acid, also methanesulphonic, ethanesulphonic, hydroxyethanesulphonic, ethylenedisulphonic, halobenzenesulphonic, toluenesulphonic and naphthalenesulphonic acid or sulphanilic acid, also methionine, tryptophan, lysine or arginine, and ascorbic acid.

The formation of the salts and the conversion of salts into the free compounds are carried out in a manner known per se. For example, the acid addition salts are obtained by treatment with an acid suitable for salt formation, such as one of those mentioned above, while salts can be converted into the free compounds by treatment with basic agents, such as inorganic hydroxides, carbonates and hydrogen carbonates, or organic bases and ion exchangers. These salts with the above-mentioned acids, or other salts, such as, for example, oxalates or picrates, can also be used for the purification of the resulting compounds by converting the free compounds into salts, separating these off and recovering the free compounds from the salts again. Owing to the close relationship between the compounds in free form and in the form of their salts, hereinbefore and hereinafter the free compounds should be understood as meaning also the corresponding salts, where appropriate and expedient.

The invention relates also to those forms of the process according to which a starting material is used in the form of a derivative, for example a salt, or is formed under the reaction conditions.

In the processes of the present invention, it is preferable to use those starting materials which result in the compounds described at the beginning as being especially valuable.

The present invention also includes the use of the compounds of the formula I and their salts, alone or together with adjuncts, and also in combination with other active ingredients, as agents for the therapeutic (both curative and preventive) treatment of diseases or pathological conditions that are indicated or caused, for example, by an elevated content of cholesterol and/or triglycerides in the blood, especially in the blood serum. The active ingredients according to the invention are administered in therapeutically effective amounts, preferably in the form of pharmaceutical compositions together with customary pharmaceutical carrier materials and/or adjuncts, to the warm-blooded animal requiring treatment, especially man. Depending on the species, body weight, age and individual condition, and depending on the mode of administration and especially also on individual condition, there are administered, for example, to warm-blooded animals daily doses corresponding to from approximately 1 to approximately 100 mg, especially from approximately 3 to approximately 50 mg, per kg body weight, which doses can be exceeded in severe cases. Accordingly, the invention also includes the corresponding method of medical treatment.

The invention relates, in addition, to pharmaceutical compositions that contain the compounds of the present invention as active ingredients, and to processes for their manufacture.

The pharmaceutical preparations according to the invention are for enteral, such as peroral or rectal, administration, and also for parenteral administration to warm-blooded animal. Corresponding dosage unit forms, especially for peroral administration, for example dragées, tablets or capsules, contain preferably from approximately 50 to approximately 500 mg, especially from approximately 100 to approximately 300 mg, of the active ingredient together with pharmaceutically acceptable carriers and/or adjuncts.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes prepared, for example, from corn, wheat, rice or potato starch, gelatine, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores may be provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine and also soft sealed capsules consisting of gelatine and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

Suitable rectally administrable pharmaceutical preparations are, for example, suppositories that consist of a combination of the active ingredient and a suppository base material. Suitable suppository base materials are, for example, natural or synthetic triglycerides, paraffin hydrocarbons, polyethylene glycols or higher alkanols.

Suitable for parenteral administration are especially aqueous solutions of an active ingredient in water-soluble form, for example a water-soluble salt, or aqueous injection suspensions that contain viscosity-increasing substances, for example sodium carboxymethylcellulose, sorbitol and/or dextran, and optionally stabilisers. The active ingredient, optionally together with adjuncts, can also be in the form of a lyophilisate and can be dissolved by the addition of suitable solvents before parenteral administration.

The pharmaceutical preparations of the present invention can be manufactured in a manner known per se, for example by means of conventional mixing, granulating, confectioning, dissolving or lyophilising processes. For example, pharmaceutical preparations for oral use can be obtained by combining the active ingredient with solid adjuncts, optionally granulating a resulting mixture and processing the mixture or granulate, if desired or necessary after the addition of suitable adjuncts, to form tablets or dragée cores.

The following Examples illustrate the invention described above but do not limit its scope in any way. Temperatures are given in degrees Celsius.

EXAMPLE 1

8-O,N- and 8-O,21-O-dipivaloyl-3-[4-(2,4,6-trimethylbenzyl)-1-piperazinyl]-rifamycin S 35.5 ml of pivaloyl chloride (10.5 equivalents) are added dropwise to a solution of 25 g of 3-[4-(2,4,6-trimethylbenzyl)-1-piperazinyl]-rifamycin S in 250 ml of pyridine and the whole is stirred for 8 hours at room temperature until the starting material can no longer be detected in a thin-layer chromatogram. 150 ml of methanol are then added to the solution and the whole is stirred for 1 hour at room temperature in order to decompose excess pivaloyl chloride and is then concentrated to dryness by evaporation. The residue is taken up in 300 ml of methylene chloride, the solution is filtered and the filtrate is extracted with 300 ml of water. The aqueous phase is adjusted to pH 3 to 4 with 1N hydrochloric acid and extracted three times with methylene chloride. The combined methylene chloride extracts are washed three times using 100 ml of water each time, dried, and concentrated to dryness by evaporation. The residue is applied to a column of 1000 g of silica gel and eluted with a 1:4 mixture of ethyl acetate and cyclohexane. The first fractions contain the 8-O,21-O-dipivaloyl-3-[4-(2,4,6-trimethylbenzyl)-1-piperazinyl]-rifamycin S which is obtained in the form of violet-brown crystals having a melting point of 135°–145° C. (decomposition) by further chromatography on silica gel and crystallisation from diethyl ether. The subsequent fractions contain the main product of the reaction: 8-O,N-dipivaloyl-3-[4-(2,4,6-trimethylbenzyl)-1-piperazinyl]-rifamycin S which, when crystallised from diethyl ether, forms reddish-violet crystals having a melting point of 157°–163° C.

Physical characteristics (a) 8-O,21-O-dipivaloyl compound:

ultraviolet absorption spectrum: (in ethanol) [$\lambda_{max}$ ($\epsilon$)]: 218 (36400), 258 (shoulder), 318 (shoulder), 354 (8800), 517 (1800) nm.

mass spectrum: m/e=1080 (M$^+$+H) in accordance with the empirical formula $C_{61}H_{81}N_3O_{14}$.

| $^1$H-NMR (in CDCl$_3$) [ppm (allocation)]: | | |
|---|---|---|
| 6.83 | s | (2H at the aromatic ring of the benzyl radical) |
| 5.2 | dd | (H-21) |
| 2.37<br>2.27 | } s | (aromatically bonded methyl groups) |
| 3.48 | AB | (methylene of the benzyl radical) |
| 1.47<br>1.42 | } s | (methyl groups of the pivaloyl radicals) |
| 0.95<br>0.85<br>0.70<br>0.18 | } s | (4H of methyl groups or ansa ring) |
| $^{13}$C-NMR (in CDCl$_3$) [ppm (allocation)]: | | |
| 179.2 | 1C | (pivaloyl-carbonyl) |
| 176.8 | 1C | (pivaloyl-carbonyl) |
| 27.3<br>27.2 | 3C<br>3C | } (methyl groups of the pivaloyl radicals) |
| 53.2<br>49.0 | 2C<br>2C | } (methylene groups of the piperazine radical) |
| 56.0 | 1C | (methylene of the benzyl radical) |
| 173.5<br>135.6<br>131.1<br>128.6<br>20.4 | 2C<br>1C<br>1C<br>2C<br>3C | } (trimethylphenyl) |

(b) 8-O,N-dipivaloyl compound:

ultraviolet absorption spectrum: (in ethanol) [$\lambda_{max}$ ($\epsilon$)]: 264 (31880), 320 (shoulder), 350 (shoulder), 524 (2200) nm.

mass spectrum: m/e=1080 (M$^+$+H) in accordance with the empirical formula for $C_{61}H_{81}N_3O_{14}$.

infra-red absorption spectrum: (in CH$_2$Cl$_2$): 3500, 2960, 2940, 1735, 1710, 1640, 1600, 1565 cm$^{-1}$, no amide-NH— present.

| | | ¹H-NMR (CDCl₃) [ppm (allocation)]: |
|---|---|---|
| 6.83 | s | (2H of the aromatic ring of the benzyl radical) |
| 3.45 | AB | (methylene of the benzyl radical) |
| 3.05 | m | (H-21) |
| 2.33<br>2.26 | } s | (3 methyl groups at the benzyl radical) |
| 1.48<br>1.44 | } s | (6 methyl groups of the pivaloyl) |
| 1.07<br>0.96<br>0.81<br>0.24 | } d | (4H of methyl groups or ansa ring) |
| | | ¹³C-NHR (in CDCl₃): |
| 190.4 | 1C | (pivaloyl-carbonyl) |
| 179.0 | 1C | (pivaloyl-carbonyl) |
| 45.3 | 1C | (quaternary C of the pivaloyl radicals) |
| 40.5 | 1C | (quaternary C of the pivaloyl radicals) |
| 29.4 | 3C | (3 methyl groups of the pivaloyl radicals) |
| 27.7 | 3C | (3 methyl groups of the pivaloyl radicals) |
| 52.5<br>50.2 | 2C<br>2C | } (4 methylene groups of the piperazine) radical) |
| 54.9 | 1C | (methylene of the benzyl radical) |
| 137.5<br>135.7<br>131.3<br>128.7<br>19.7 | 2C<br>1C<br>1C<br>2C<br>3C | } (2,4,6-trimethylphenyl) |

The starting material can be obtained in the following manner:

(a) 30 g of N-(2,4,6-trimethylbenzyl)-piperazine are added to a solution of 50 g of rifamycin S in 500 ml of dioxan and the whole is left to stand at room temperature for 18 hours. The mixture is then acidified by the addition of a 10% aqueous citric acid solution and the reaction product is taken up in methylene chloride. After the methylene chloride extract has been dried and concentrated by evaporation, the dark-coloured residue is dissolved in ethanol, and then aqueous ascorbic acid is added dropwise thereto. The 3-[4-(2,4,6-trimethylbenzyl)-1-piperazinyl]-rifamycin SV is obtained in the form of yellow crystals having a melting point of 178°–181° C. (partial decomposition).

(b) A solution of 10 g of the product prepared according to (a) in 200 ml of methylene chloride is stirred intensively for 5 minutes with 10 g of finely ground manganese dioxide. The solid portions are filtered off and the filtrate is concentrated to dryness by evaporation, yielding the amorphous blue-black 3-[4-(2,4,6-trimethylbenzyl)-1-piperazinyl]-rifamycin S which is processed further without further purification.

EXAMPLE 2

8-O,N-dipivaloyl-3-[4-(2,6-dimethyl-4-tert.-butylbenzyl)-1-piperazinyl]-rifamycin S In a manner analogous to that described in Example 1, starting from 3-[4-(2,6-dimethyl-4-tert.-butylbenzyl)-1-piperazinyl]-rifamycin S, the title compound is obtained in the form of a solid without a clearly defined melting point;

mass spectrum: m/e=1121 (M⁺) in accordance with the empirical formula for $C_{64}H_{87}N_3O_{14}$;

ultraviolet absorption spectrum: (in ethanol) [λ$_{max}$ (ε)]: 263 (29960); 324 (shoulder); 360 (shoulder); 526 (2000) nm.

infra-red absorption spectrum: (in methylene chloride): 3500, 2970, 1735, 1675, 1640, 1600, 1570 cm⁻¹.

| | | ¹H-NMR (in CDCl₃) [ppm (allocation)]: |
|---|---|---|
| 7.00 | s | (2H at the aromatic ring of the benzyl radical) |
| 3.43 | AB | (methylene of the benzyl radical) |
| 2.35 | s | (3 methyl groups at the aromatic ring) |
| 1.48<br>1.44 | } s | (6 methyl groups of the pivaloyl radicals) |

The starting material can be manufactured in the following manner:

3 g of N-(2,6-dimethyl-4-tert.-butylbenzyl)-piperazine are added to a solution of 5 g of 3-bromorifamycin S in 50 ml of tetrahydrofuran and the whole is left to stand for 30 minutes at 20°. The mixture is then acidified by the addition of aqueous citric acid solution and the reaction product is taken up in methylene chloride. After the methylene chloride extract has been dried and concentrated by evaporation, a dark-coloured residue remains behind; the residue is dissolved in methanol, and aqueous ascorbic acid is added dropwise thereto. The 3-[4-(2,6-dimethyl-4-tert.-butylbenzyl)-1-piperazinyl]-rifamycin SV is obtained in the form of yellow-coloured crystals, melting point 260°. Treatment with manganese dioxide as described under (b) in Example 1 yields the desired starting material of the S series.

EXAMPLE 3

In analogous manner it is possible to obtain the following compounds of the formula I:

8-O,21-O-di-(2,2-dimethylbutyryl)-3-[4-(2,4,6-trimethylbenzyl)-1-piperazinyl]-rifamycin S and 8-O,N-di-(2,2-dimethylbutyryl)-3-[4-(2,4,6-trimethylbenzyl)-1-piperazinyl]-rifamycin S or a mixture thereof;

8-O,21-O-di-(2-ethyl-2-methylbutyryl)-3-[4-(2,4,6-trimethylbenzyl)-1-piperazinyl]-rifamycin S and 8-O,N-di-(2-ethyl-2-methylbutyryl)-3-[4-(2,4,6-trimethylbenzyl)-1-piperazinyl]-rifamycin S or a mixture thereof;

8-O,21-O-di-(2,2-diethylbutyryl)-3-[4-(2,4,6-trimethylbenzyl)-1-piperazinyl]-rifamycin S and 8-O,N-di-(2,2-diethylbutyryl)-3-[4-(2,4,6-trimethylbenzyl)-1-piperazinyl]-rifamycin S or a mixture thereof;

8-O,21-O-di-(2,2-dimethylvaleryl)-3-[4-(2,4,6-trimethylbenzyl)-1-piperazinyl]-rifamycin S and 8-O,N-di-(2,2-dimethylvaleryl)-3-[4-(2,4,6-trimethylbenzyl)-1-piperazinyl]-rifamycin S or a mixture thereof;

8-O,21-O-di-(2-ethyl-2-methylvaleryl)-3-[4-(2,4,6-trimethylbenzyl)-1-piperazinyl]-rifamycin S and 8-O,N-di-(2-ethyl-2-methylvaleryl)-3-[4-(2,4,6-trimethylbenzyl)-1-piperazinyl]-rifamycin S or a mixture thereof;

8-O,21-O-di-(2,2-diethylbutyryl)-3-[4-(2,6-dimethyl-4-tert.-butylbenzyl)-1-piperazinyl]-rifamycin S and 8-O,N-di-(2,2-diethylbutyryl)-3-[4-(2,6-dimethyl-4-tert.-butylbenzyl)-1-piperazinyl]-rifamycin S or a mixture thereof.

EXAMPLE 4

Capsules containing 250 mg of 8-O,N-dipivaloyl-3-[4-(2,4,6-trimethylbenzyl)-1-piperazinyl]-rifamycin S can be manufactured as follows:

| Composition (for 1000 capsules): | |
|---|---|
| 8-O,N-dipivaloyl-3-[4-(2,4,6-trimethyl-benzyl)-1-piperazinyl]-rifamycin S | 250.0 g |
| corn starch | 50.0 g |
| polyvinylpyrrolidone | 15.0 g |
| magnesium stearate | 5.0 g |
| ethanol | q.s. |

The active ingredient and the corn starch are mixed together and moistened with a solution of the polyvinylpyrrolidone in 50 g of ethanol. The moist mass is pressed through a sieve having a mesh width of 3 mm and dried at 45°. The dry granulate is passed through a sieve of 1 mm mesh width and mixed with 5 g of magnesium stearate. 0.320 g portions of the mixture are introduced into size 0 dry-fill capsules.

In analogous manner it is also possible to use 8-O,21-O-dipivaloyl-3-[4-(2,4,6-trimethylbenzyl)-1-piperazinyl]-rifamycin S or a mixture thereof with the corresponding 8-O,N-dipivaloyl compound.

EXAMPLE 5

250 g of an active ingredient according to Example 1 or 2 and 1750 g of finely ground suppository base material (for example cocoa butter) are thoroughly mixed and then melted. 1000 suppositories of 2 g are cast from the melt which is kept homogeneous by stirring. Each suppository contains 250 mg of active ingredient.

We claim:

1. A compound of the formula

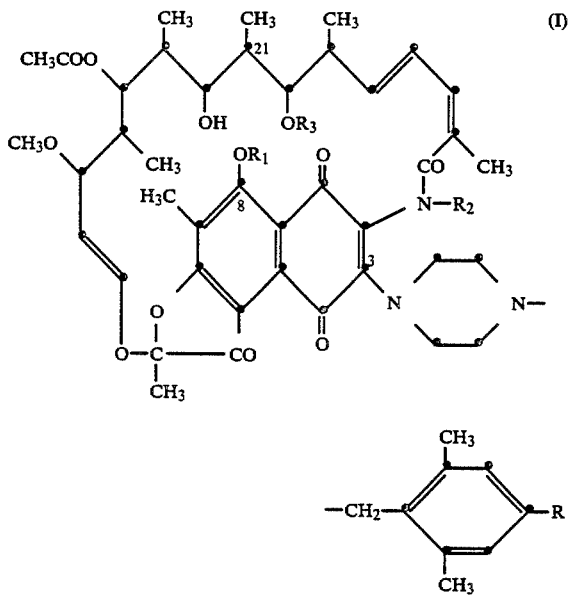

in which R represents lower alkyl, $R_1$ represents tri-lower alkylmethylcarbonyl, and one of the radicals $R_2$ and $R_3$ represents tri-lower alkylmethylcarbonyl and the other represents hydrogen, or a pharmaceutically acceptable salt thereof.

2. The compound of the formula I according to claim 1, in which R represents lower alkyl, and in which $R_1$ and $R_2$ represent tri-lower alkylmethylcarbonyl in which lower alkyl contains up to and including 2 carbon atoms, and $R_3$ represents hydrogen, or in which $R_1$ and $R_3$ represent tri-lower alkylmethylcarbonyl in which lower alkyl contains up to and including 2 carbon atoms, and $R_2$ represents hydrogen, or a pharmaceutically acceptable salt thereof.

3. The compound of the formula I according to claim 1, in which R is methyl, and $R_1$ and $R_2$ represent pivaloyl and $R_3$ represents hydrogen, or $R_1$ and $R_3$ represent pivaloyl and $R_2$ represents hydrogen, or a pharmaceutically acceptable salt thereof.

4. The compound of the formula I according to claim 1, 8-O,21-O-dipivaloyl-3-[4-(2,4,6-trimethylbenzyl)-1-piperazinyl]-rifamycin S or a pharmaceutically acceptable salt thereof.

5. The compound of the formula I according to claim 1, 8-O,N-dipivaloyl-3-[4-(2,4,6-trimethylbenzyl)-1-piperazinyl]-rifamycin S or a pharmaceutically acceptable salt thereof.

6. A Pharmaceutically acceptable salt of the compounds of the formula I according claim 1.

7. A process for the manufacture of a compound of the formula I according to claim 1, comprising treating a compound of the formula

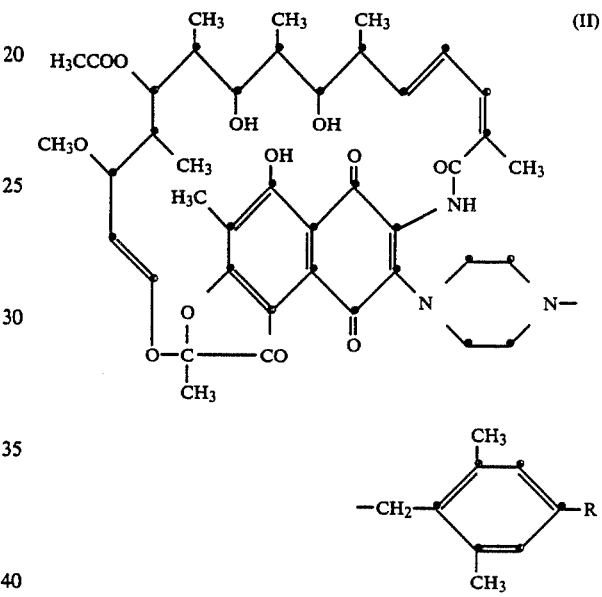

with an acylating agent that introduces a tri-lower alkylmethylcarbonyl radical $R_1$ and $R_2$ or $R_1$ and $R_3$ into position 8, and into position 21 or the ring amide nitrogen atom, and, if desired, a mixture of isomers obtained according to the process is separated, and/or a salt obtained according to the process is converted into the free compound or into a different salt, and/or a free compound obtained according to the process is converted into a salt.

8. The process of claim 7 wherein said acylating agent is a tri-lower alkylmethylcarboxylic acid or reactive derivative thereof.

9. The process of claim 8 wherein acylating agent is a tri-lower alkylmethylcarboxylic acid anhydride.

10. The process of claim 9 wherein said acid anhydride is a mixed acid anhydride.

11. The process of claim 8 wherein said acylating agent is a tri-lower alkylmethylcarbonyl halide.

12. The process of claim 11 wherein said acylating agent is a tri-lower alkylmethylcarbonyl chloride.

13. A hypolipidaemic composition comprising a hypolipidaemically effective amount of a compound of claim 1 or a pharmaceutically acceptable salt thereof and a pharmaceutically acceptable carrier.

14. A method of reducing lipids in an animal in need thereof comprising administering to said animal a hypolipidaemically effective amount of a compound of claim 1 or a pharmaceutically acceptable salt thereof.

* * * * *